(12) United States Patent
Avila et al.

(10) Patent No.: US 8,203,606 B2
(45) Date of Patent: Jun. 19, 2012

(54) GRADIENT IMAGE PROCESSING

(75) Inventors: Thiago I. Avila, Windsor (CA); Petru S. Buse, Kitchener (CA); Joshua A. H. Walter, Baden (CA)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 690 days.

(21) Appl. No.: 12/267,066

(22) Filed: Nov. 7, 2008

(65) Prior Publication Data

US 2010/0118137 A1 May 13, 2010

(51) Int. Cl.
*H04N 9/47* (2006.01)

(52) U.S. Cl. ............. 348/125; 348/88; 348/90; 348/92; 348/126; 348/127; 348/128; 348/129; 348/130; 382/141; 382/149; 382/152

(58) Field of Classification Search .................. 348/125, 348/129–130, 88, 90, 92; 382/141, 149, 382/152

See application file for complete search history.

(56) References Cited

U.S. PATENT DOCUMENTS

| | | | |
|---|---|---|---|
| 4,001,497 A * | 1/1977 | Bosworth | 348/90 |
| 5,640,200 A | 6/1997 | Michael | |
| 5,654,977 A * | 8/1997 | Morris | 374/4 |
| 6,909,800 B2 | 6/2005 | Vaidyanathan | |
| 2006/0018514 A1* | 1/2006 | Bankhead | 382/108 |
| 2006/0222237 A1* | 10/2006 | Du et al. | 382/152 |
| 2009/0161720 A1* | 6/2009 | Pelletier | 374/4 |
| 2010/0260374 A1* | 10/2010 | Akashi et al. | 382/100 |

* cited by examiner

*Primary Examiner* — Duyen Doan
(74) *Attorney, Agent, or Firm* — Gifford, Krass, Sprinkle, Anderson & Citkowski, P.C.

(57) ABSTRACT

A method of assessing the quality of metal parts, for example through detection of defects in a metal part induced by processing the metal part, comprises acquiring a thermal image of the metal part after processing the metal part, determining a difference image by comparing the thermal image to a reference image, the difference image being related to temperature differences between temperature data represented by the thermal image and by the reference image, and determining a gradient image using the difference image, the gradient image representing temperature difference gradients within the difference image. An example apparatus comprises a camera, such as a thermal camera, an image processor, and an output device such as a display.

13 Claims, 8 Drawing Sheets

GRADIENT IMAGE PROCESSING

FIELD OF THE INVENTION

The present invention relates to image processing, in particular to image processing of thermal images to assist defection of defects in formed metal parts.

BACKGROUND OF THE INVENTION

Defects may occur during the forming of metal parts, such as the stamping of metal sheets into panels. Defects may include elongation defects, such as strains greater than an acceptable threshold, tears, voids, and the like. Defects may not be immediately apparent using visual inspection or other conventional approach. A defective part may then be further processed before the defect is discovered. Also, if defects are not discovered at the time of forming the part, conditions may remain for creation of similar defects in other parts. Hence, it is extremely useful to detect defects in formed parts, such as formed metal parts, soon after they are discovered.

SUMMARY OF THE INVENTION

A method of detecting defects in a metal part formed during processing of the metal part comprises acquiring a thermal image of the metal part after processing, determining a difference image by comparing the thermal image to a reference image, and determining a gradient image using the difference image. The difference image correlates to temperature differences between spatial temperature distributions represented by the thermal image and by the reference image. The gradient image correlates to the rate of change in temperature differences within the difference image.

The term "acquired image" is used to refer to an image, such as a thermal image, collected from a part, such as a metal part, passing through processing equipment. The term "reference image" refers to an image against which the acquired image may be compared, for example a previously collected thermal image of a reference part. The acquired and reference images can be compared (e.g. subtracted from each other) so as to determine a difference image. A difference image may represent the spatial distribution of temperature differences between the current part (the part currently being processed) and the reference part, as determined by subtracting the reference image from the acquired image. The difference image may determined by subtracting reference temperature data represented by the reference image from temperature data represented by the thermal image, so as to obtain a spatial distribution of the temperature differences between the reference part and the part being processed, from which the acquired image is obtained.

Methods according to examples of the present invention include methods of detecting defects in metal parts after a metal forming process, such as detection of elongation defects and split defects in a stamped metal part.

The reference image may be a reference thermal image collected from a reference part, for example after processing the reference part using the same or similar equipment, and after determining that the reference part was substantially defect-free. For example, the thermal image of the current part and the reference part may both be acquired within 5 seconds of processing the respective part, for example within 3 seconds of processing the respective part. The delay between processing and imaging may be substantially identical for reference and current parts.

A thermal image of a current part may be aligned with the reference image before determining the difference image, for example using edge detection to locate edges or other features (such as holes) of the parts. Reference to an "image" is not intended to suggest that the image is visually presented, as image processing may occur without visual presentation of the image. For example, the term "image" may be used to describe data representative of the spatial variation of temperature, difference temperature, or gradient of the difference temperature over a part.

An output device may be used to display a filtered image, for example an image indicating regions having a difference temperature gradient greater than a threshold value, allowing reliable identification of defects.

An apparatus for assisting the detection of defects in a metal part after processing comprises a camera, operable to acquire a thermal image of the metal part, and an image processing device, operable to compare the thermal image with a reference thermal image so as to determine a difference image, the difference image representing temperature differences between temperatures represented by the thermal image and a reference temperatures represented by the reference image. An image processing device may be further operable to determine a gradient image, the gradient image representing rates of change of temperature differences within the difference image. The apparatus may further comprise an output device providing an indication if values within the gradient image exceed a threshold value, so as to assist detection of defects within the metal part. The camera may be a thermal camera, such as an IR camera.

The image processing device may be provided by an electronic circuit comprising a processor, a memory, a data input port, and a display output, the processor being operable to execute an algorithm, the algorithm determining the gradient image, the data input port receiving the thermal image from the camera, and the reference image being stored in the memory. The electronic circuit may be provided by a computer. The output device may be a display, the image processor being operable to show the gradient image and/or a filtered version thereof on the display.

The occurrence of split and elongation defects during a metal forming process may not be detected immediately using conventional methods, and defects may end up in finished products. Examples of the present invention allow for automatic detection of these defects soon after the process. Detection of one or more defects may be presented to a human operator using a visual and/or audible alert. In some examples, equipment operation may be stopped automatically after detection of a defect or other problem in a part, for example using an electrical signal transmitted to the processing equipment from an image processing apparatus.

Shifts in image mean temperature can occur as forming tools heat up during a production run, so that the image mean temperature increases with time. This shift can be greater than the differences in temperature observed between normal and defective parts. Thus a simple temperature increase threshold, relative to a constant baseline, cannot be used to accurately differentiate normal and defective parts. A point of failure is typically at a point of highly local deformation, so that the rate of chance in deformation (deformation gradient) approaching a defect is higher than normal. As temperature increase is proportional to deformation, the temperature gradient near a defect is also higher than normal. A user defined threshold for maximum allowable temperature gradient can be used, yielding accurate differentiation between normal and defective parts.

During forming, areas of increased deformation exhibit a higher temperature than the surrounding metal. Examples of the present invention use one or more thermal imaging cameras in combination with a novel image processing algorithm to differentiate normal and defective parts. For example, defect can be detected within one cycle of a press or other forming apparatus, allowing the equipment can be stopped and any problem solved before more defective parts are manufactured, and before the first defective part is further processed.

Examples of the present invention allow detection of split and elongation defects in any sheet metal drawing process, including automotive manufacture and other industries.

DETAILED DESCRIPTION OF THE INVENTION

Figure 1:
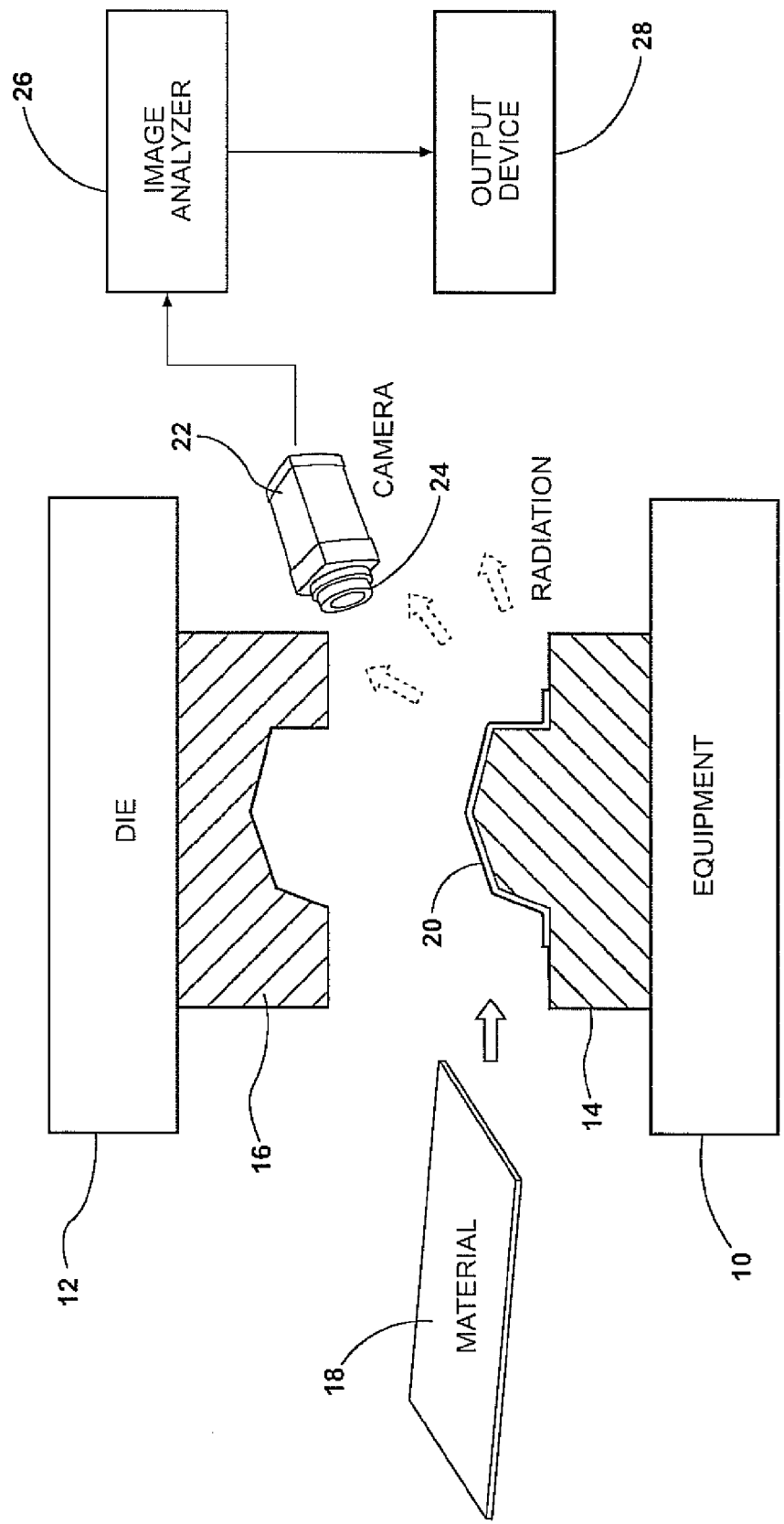
FIG. 1 shows an apparatus comprising a camera, an image analyzer configured to determine a temperature gradient image, and an output device.

Examples of the present invention relate to thermal gradient imaging processes that can assist the detections of defects in a part after processing of the part. In some examples, the part is a metal part, such as a metal sheet, and examples of the invention allow detection of defects such as splits and elongation defects created during a metal forming process such as stamping.

In some examples discussed below, the stamping of metal sheets is discussed. However, these examples are not intended to be limiting and examples of the present invention includes methods and apparatus for the processing of other parts, including forming processes such as stamping, rolling, extrusion, and in particular metal forming processes.

The elongation of metal during a forming process typically induces local heating. As a metal is plastically deformed, heat is generated proportional to strain. A strain is that is larger than normal may correspondingly produce heat energy greater than normal. However, heating up of the processing equipment during normal operation may impart additional heat energy to the part, so that it can be difficult to set a detection threshold for excess heating that corresponds to a defect condition without also false positive defect detections also occurring due to the heating up of the processing equipment as it runs. Tears or voids in the metal can appear cooler than the surroundings in a thermal image.

Using conventional methods, such as visual inspection, defects may not be immediately apparent. A defective part may then be further processed, or even end up in a finished product, before the defect is discovered. The defect may be discovered after sale of a product, leading to safety issues, recall expenses, and loss of customer confidence. Even if visual inspection is sufficient to identify splits, there may be insufficient time to complete a visual inspection without significantly slowing production, certain elongation defects may be difficult to see, defects may be intermittent so that sampling approaches may be unsuccessful, and there may be ergonomics concerns such as the threat of repetitive strain injury for any human-based inspection process.

In some examples of the present invention, a thermal gradient image process includes acquiring a thermal image after the metal forming process has taken place, preferably before cooling and/or thermal dissipation and equalization effects greatly reduce the effects of any defects on the thermal image. For example, an image can be acquired before any hot spots in the current part have adequate time to cool. The acquired image may then be aligned with a reference image, such as an image of a substantially defect-free part, and the reference image can be subtracted from the acquired image (or vice versa). A temperature gradient image (or "gradient image") is then determined, representing the rate of change in temperature versus spatial coordinate of the imaged part. The gradient image may represent, for example, changes in temperature per unit distance in one or more directions, such as orthogonal directions. A mask is optionally applied to the image to remove edge effects. A high pass filter can be used to remove large-scale temperature variations. In this context, large scale temperature variations occur over a spatial extent substantially greater than that of the defects of interest, if appropriate. The gradient image highlights rapid changes in temperature, and is then compared with a user defined threshold for maximum allowable temperature gradient. Parts with temperature gradients in excess of the maximum allowable temperature gradient are flagged as containing an unacceptable split or elongation, and can be rejected before continuing through subsequent value adding processes.

The acquired image (the image obtained from the current part shortly after the forming process is complete) and the reference image (for example, an image of a previously image acceptable part, which may be termed a reference part) can be aligned before subtraction to reduce or substantially eliminate the effects of movement between the part and the camera, for example due to vibration from the metal forming process. Image alignment and subtraction can remove the effects of background noise, and allows the differences between the acquired image and reference image to be represented by a difference image. A gradient image can then be determined as the spatial variation of thermal gradient of the difference image.

Examples of the present invention can be applied to defect detection after the forming of any material showing discernable thermal effects caused by the forming process, including the molding and stamping of plastics.

FIG. 1 shows an example configuration for forming a metal part, comprising equipment in the form of a press with lower and upper portions 10 and 12 respectively, die with lower and upper portions 14 and 16 respectively, and part 20. The die and part are shown in cross-section, the part 20 being formed into a desired shape using the die.

FIG. 1 further illustrates an apparatus according to an example of the present invention, including camera 22, radiation being detected through lens 24, image analyzer 26, and output device 28.

The camera 22 is operable to acquire an image data of the part after forming process. The image analyzer 26 is operable to compare the acquired image data with reference image data to obtain difference image data. The difference image data can be determined so as to represent the spatial distribution of a difference temperature over the part, the difference temperature being the temperature of the current part at a particular location subtracted by the temperature of a reference part at a corresponding location. The current part and the reference part may have similar shapes, and images may be aligned using edge detection or other methods to obtain alignment points or lines for each image. The image analyzer is further operable to determine gradient image data. Gradient image data can be determined as the spatial gradient of the difference temperature over the part.

For example, the acquired image data may represent a spatial variation of part temperature in one, two, or three spatial dimensions. For a part in the form of a sheet, two spatial dimensions may be used. A processing step may be used to convert spectral data obtained from the camera into temperature image data, or the camera may provide temperature data directly to the image analyzer.

In this example, the camera is a thermal camera and receives thermal radiation from the part after completion of the process, such as a metal forming process. Thermal image data is from the current part, the part that has just been processed by the equipment, preferably before cooling and/or dissipation effects significantly reduce thermal non-uniformity of the part after the process. For example, the thermal image may be acquired as soon as separation of upper and lower die parts allow thermal radiation from the desired field of view (which include the entire part or a portion thereof) to reach the camera.

The electromagnetic range of the camera can be chosen depending on the temperature of the part after forming process. In this example, the thermal camera is an IR camera. In some examples, processing equipment such as a press may have a camera, image analyzer, and output device integrated therein.

Figure 2:
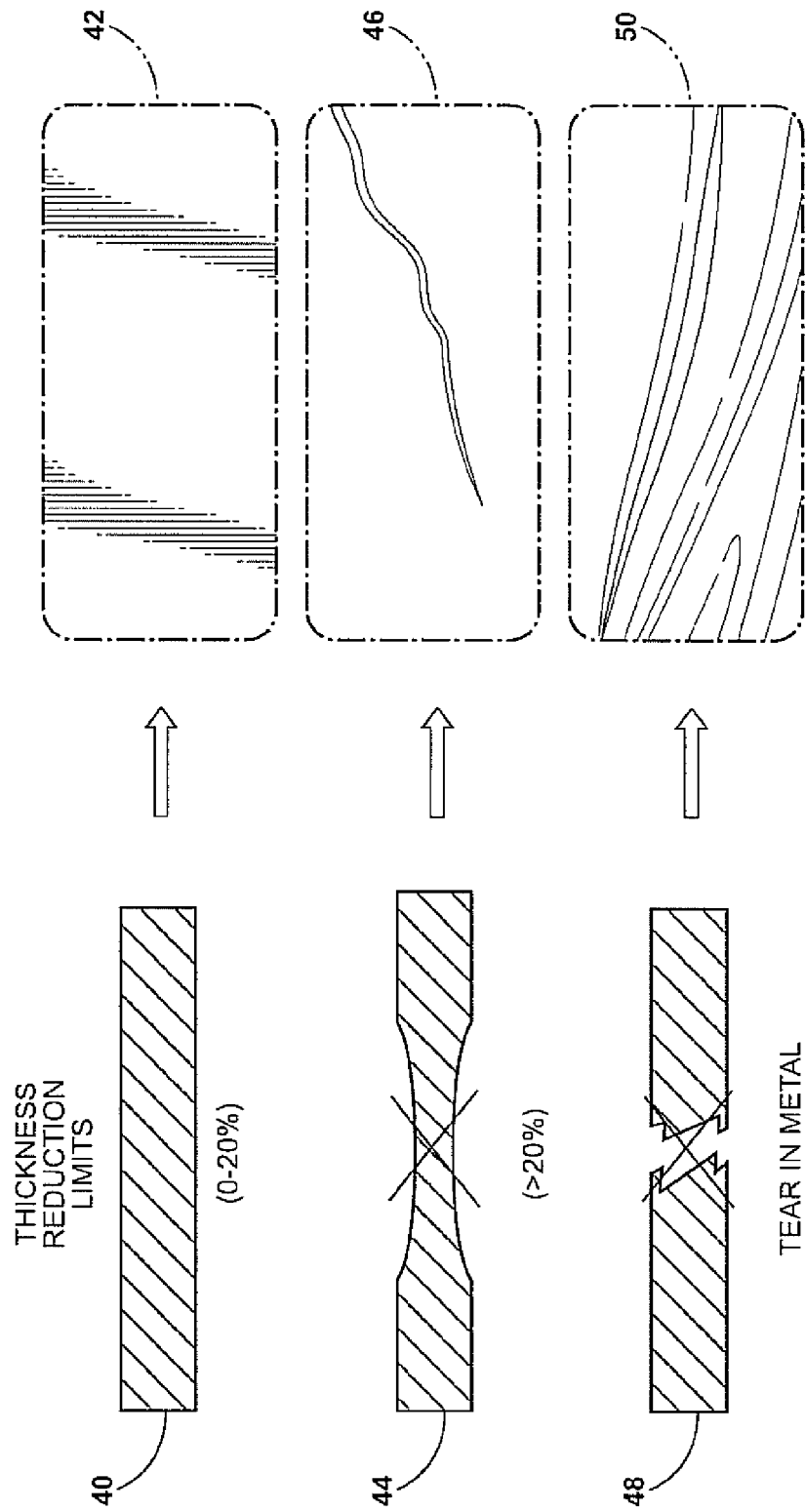
FIG. 2 illustrates a thickness reduction limit for elongation defects and tears in a metal panel, and associated visual images.

FIG. 2 illustrates thickness reduction limits. In this example, a thickness reduction in the range of 0-20% illustrated at 40 results in an acceptable formed part, shown in visual image 46. A thickness reduction of >20% shown at 44 leads to elongation defects 46, as illustrated in the visual image. However, elongation defects may be difficult to see in a visual inspection. A tear in the metal shown at 48 may be more apparent within the visual image 50.

Figure 3A:
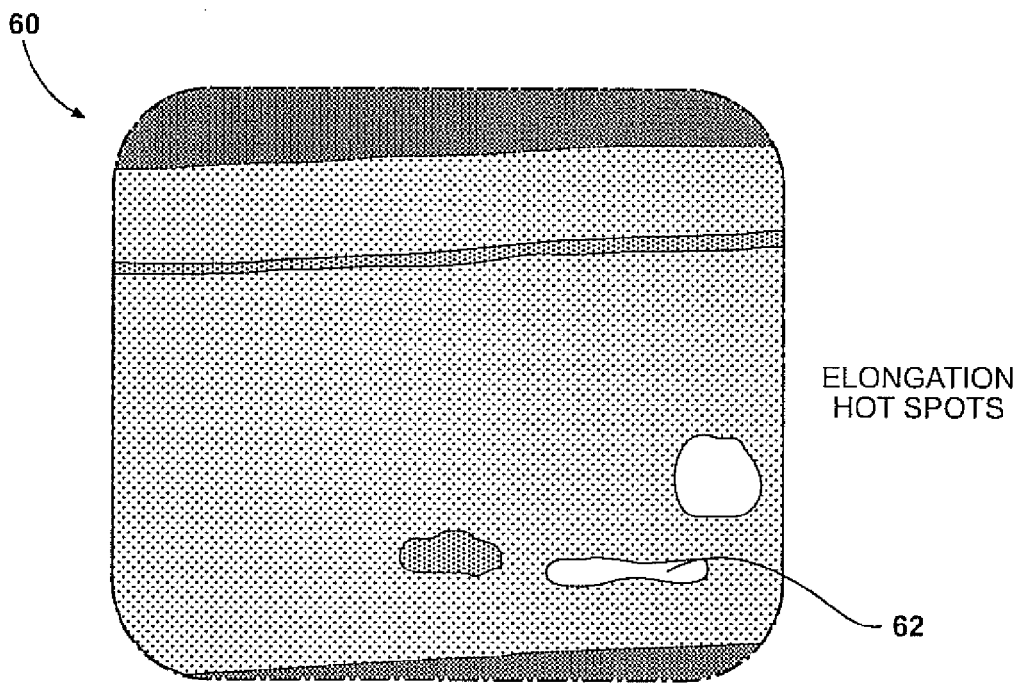
FIG. 3A illustrates an elongation hot-spot within a thermal image.

FIG. 3A illustrates an elongation hot-spot 62 within a thermal image 60.

Figure 3B:
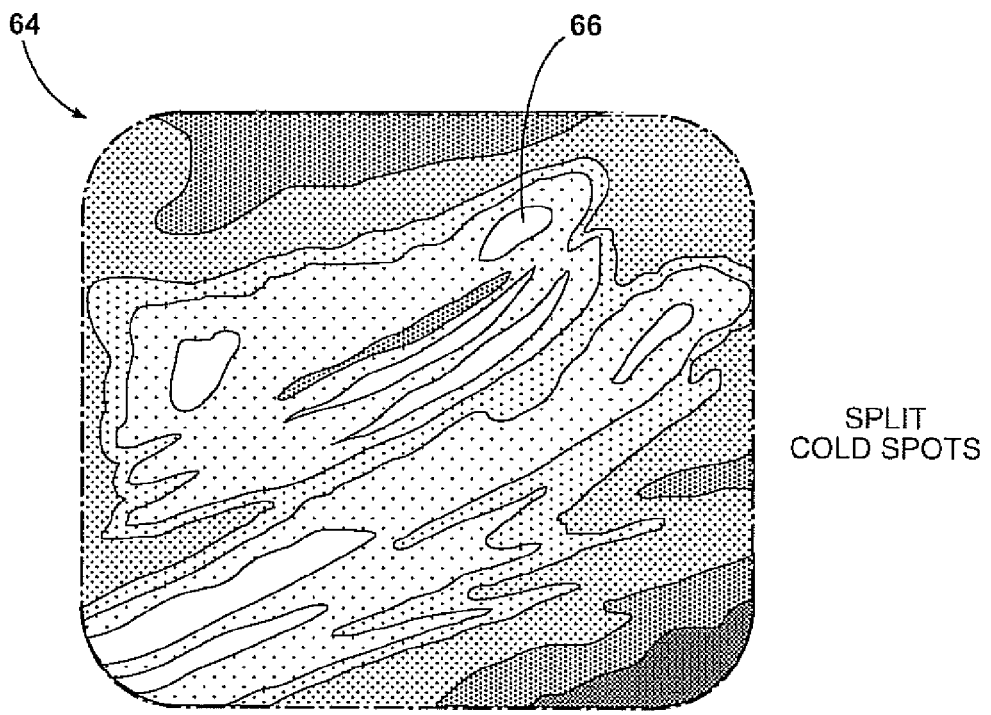
FIG. 3B illustrates a split in a metal sheet resulting in cold spots within a thermal image.

FIG. 3B illustrates a split in a metal sheet resulting in cold spots 66 within a thermal image 64. The colors (or gray scale levels) of a thermal image may be selected to emphasize the defects.

Figure 4:
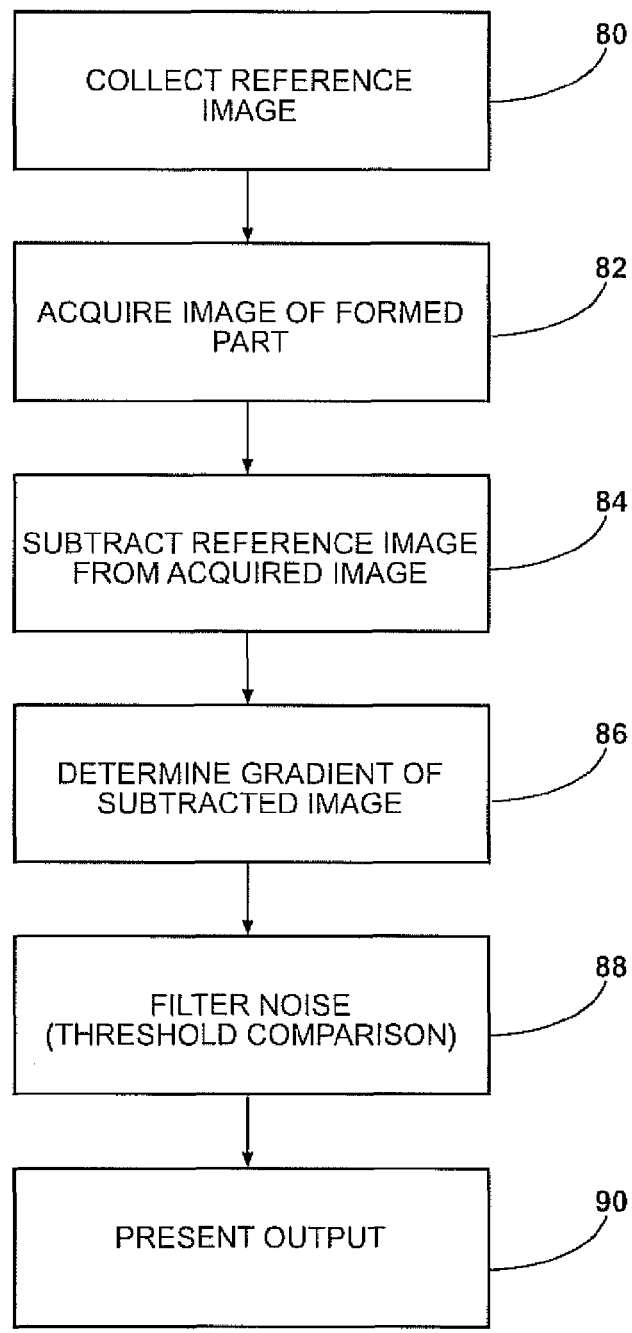
FIG. 4 illustrates a gradient image process according to an embodiment of the present invention.

FIG. 4 illustrates a gradient image process according to an embodiment of the present invention. Box 80 corresponds to collecting reference image data. Box 82 corresponds to acquiring image data for the formed part. The reference image data may correspond to a thermal image of an acceptable (e.g. substantially defect-free) reference part obtained with the same camera used to acquire the image data for the formed part. Box 84 corresponds to comparing the acquired image data (the image data for the formed part) with the reference image data to obtain difference image data. In this example, the temperature distribution corresponding to the reference image data is subtracted from the temperature difference corresponding to the acquired image data, so that the difference image data corresponds to a subtracted image representing the temperature differences between the formed part and the reference part. The acquired image and reference image may be aligned before the subtraction step, for example using image recognition software to detect analogous structures in each image and then align the two images.

Box 86 corresponds to determining the gradient image, in this example related to the spatial distribution of changes in the difference temperature over the part. Box 88 corresponds to filtering noise from the gradient image. In this example, gradients of the difference temperature greater than a predetermined threshold are detected and may be visually presented to an equipment operator. Box 90 corresponds to presenting the output, for example to an equipment operator. In other examples, the output may be provided to the equipment in the form of a signal to stop operation. A visual output to an operator may include pass/fail indications, number and location of defects, and the like.

Figure 5:
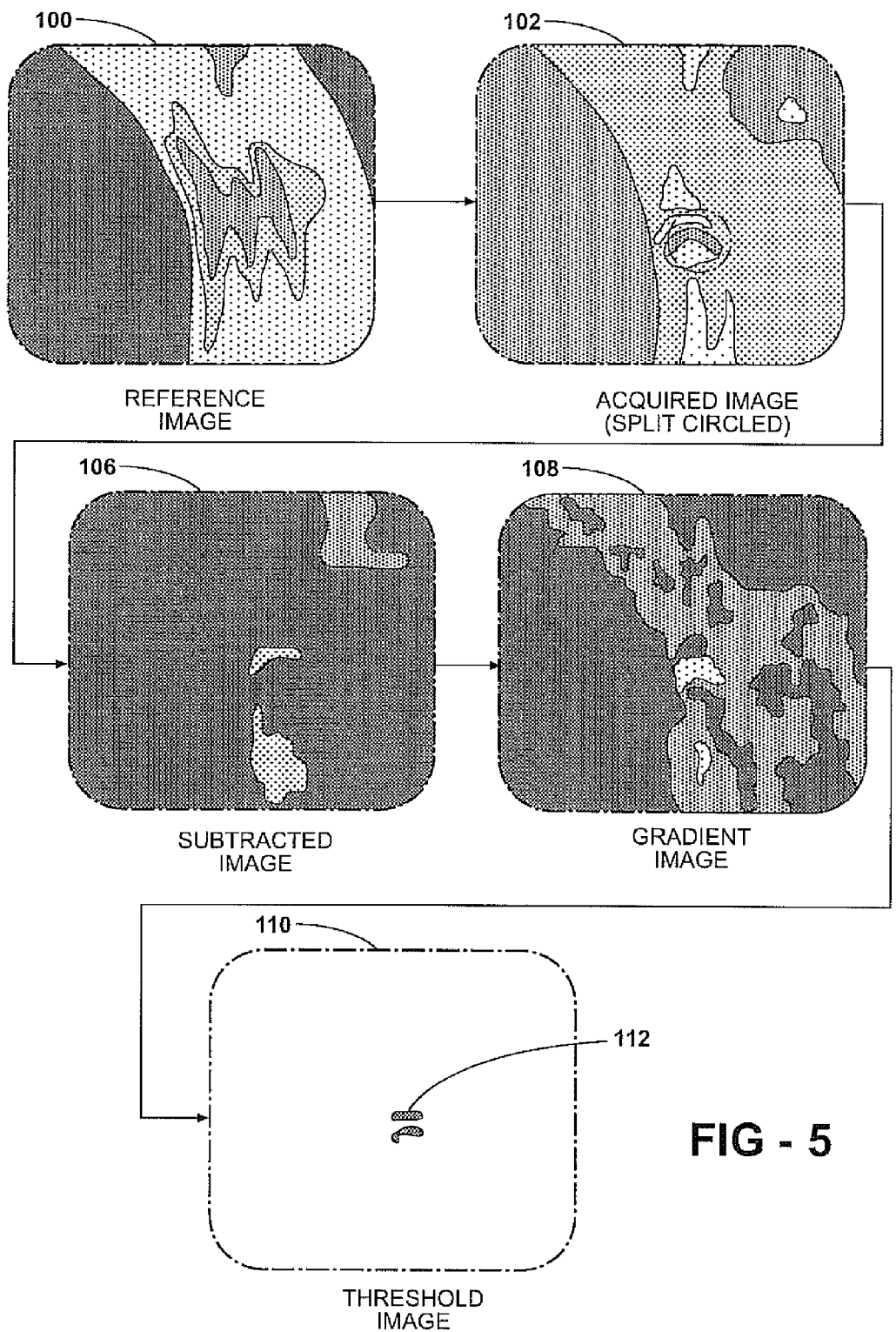
FIG. 5 illustrates a sequence of images obtained during an example gradient image process.

FIG. 5 illustrates a sequence of images obtained during an example gradient image process. The image at 100 is a thermal reference image of an acceptable reference part, obtained after forming the reference part. The image at 102 is an acquired thermal image of formed part, obtained after forming the part. The reference image and acquired image may be obtained under similar or related conditions, for example with a similar delay between part forming and image data collection. The delay may, for example, be in the range 0.01-10 seconds, more preferably 0.1-5 seconds, for example 0.1-3 seconds. However, the delay used may be chosen depending on processing conditions.

The image at 106 is the subtracted image, in which the temperature distribution of the reference part is subtracted from the temperature distribution of the formed part. A subtracted image is a type of temperature difference image. In some examples, the temperature distribution of the formed part may be subtracted from the temperature difference of the reference part.

Image 108 shows a gradient image, corresponding to the gradient of the difference temperature over the part, e.g. $\Delta(T_a-T_{ref})/\Delta s$, where $T_a-T_{ref}$ is the temperature difference between the acquired part and the reference part, and s is a spatial parameter. The gradient calculated may correspond to the difference temperature gradient along a spatial direction of maximum difference temperature gradient. In some examples, the gradient may be calculated along a predetermined spatial direction.

Image 110 shows a threshold image, after difference temperature gradients below a threshold have been removed from the image. The remaining features 112 can be used to assess the quality of the part, in particular to indicate the position, type, and severity of defects.

Example methods may further include aligning an acquired thermal image for a part and a reference thermal image, subtraction of the reference thermal image from the acquired thermal image to obtain a difference thermal image, determining a gradient thermal image representing temperature gradients within the difference thermal image, and detect defect using the difference thermal image.

An example apparatus and method, using alignment of the acquired thermal image for a formed part with the reference thermal image, were tested in a production line environment and 100% correlation with manual testing methods was found. There were 15 true negatives, 8 true positives, no false positives, and no false negatives, so that 100% of splits were detected. Heat transfer caused loss of detail, and the image data was acquired within 3 seconds of completion of the stamping process. However, other time delays between part processing and image acquisition can be used, such as delays equal to or less than approximately 5 seconds. In this example, splits with a minimum gap of 0.5 mm were reliably detected.

Figure 6A:
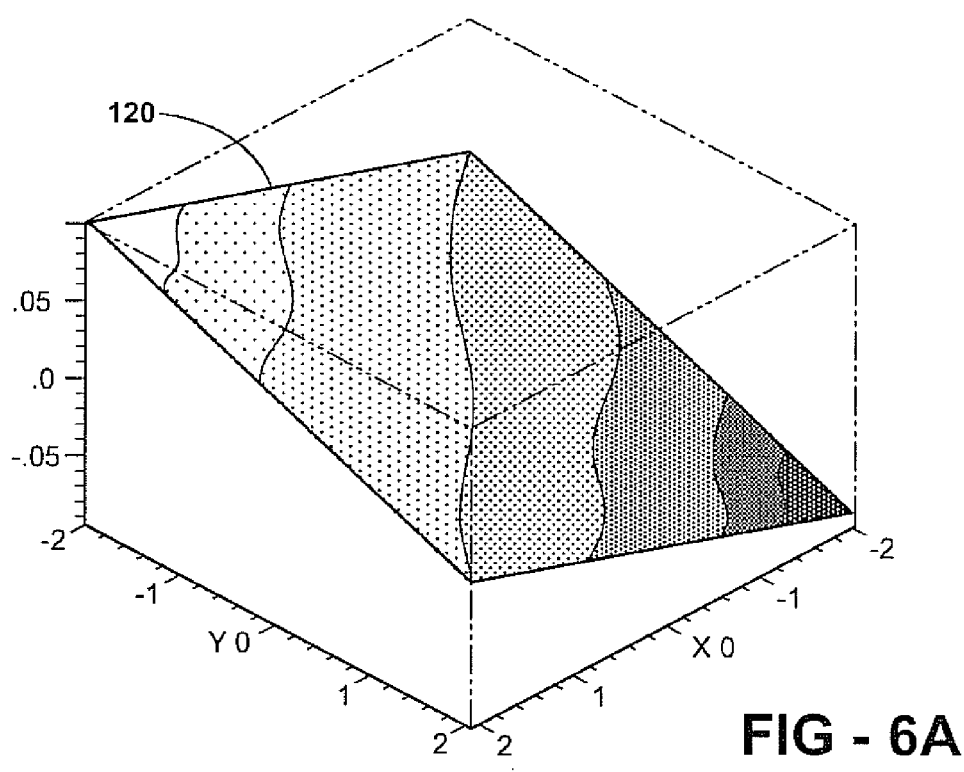
FIG. 6A shows a gradual temperature changes associated with acceptable parts after a forming process.
Figure 6B:
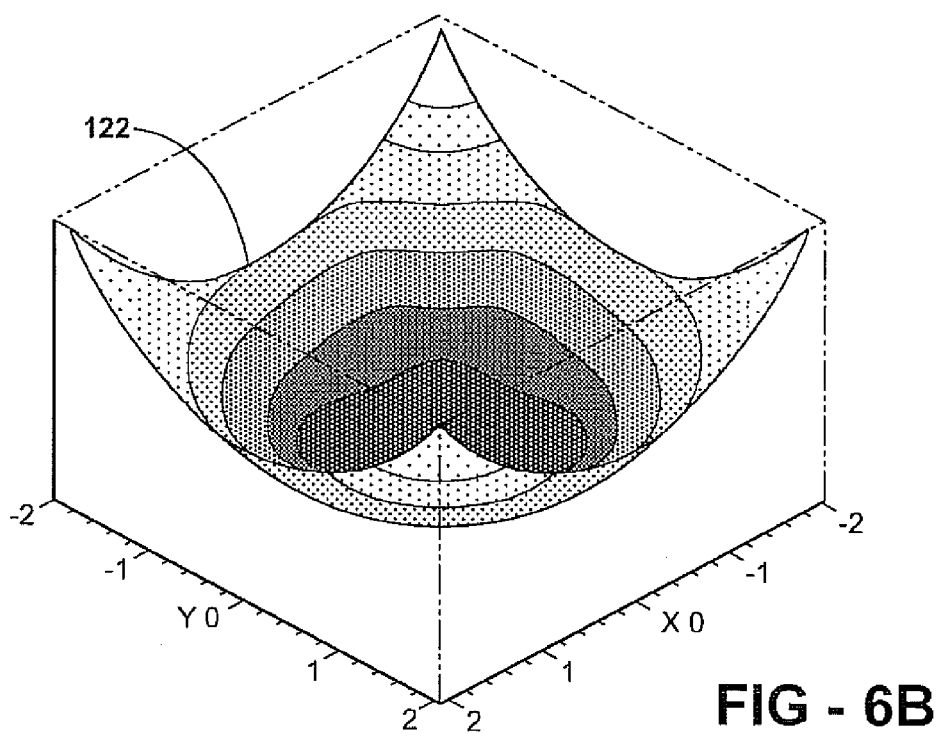
FIG. 6B shows abrupt changes in temperature that are correlated with the presence of splits and elongations after a forming process.

FIG. 6A shows a gradual temperature change that is typically associated with good parts. This type of temperature distribution may give gradient image data that may be below a predetermined threshold. FIG. 6B illustrates abrupt changes in temperature that are correlated with the presence of splits and elongations. These figures use arbitrary units and are for illustrative purposes only.

Figure 7:
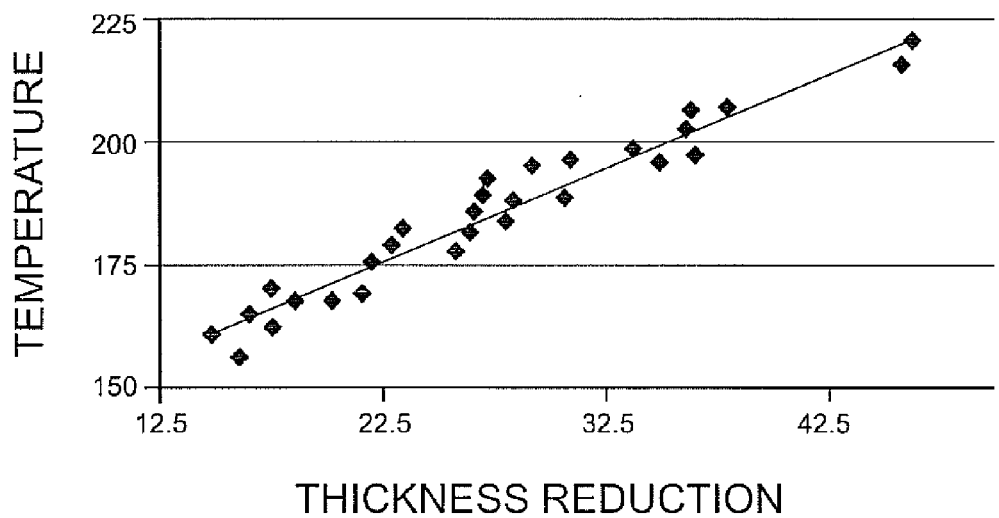
FIG. 7 illustrates a correlation determined between temperature and thickness reduction during a stamping process.

FIG. 7 illustrates a correlation between temperature of a stamped metal panel and thickness reduction during a stamping process. The data was acquired before significant cooling of the formed part had occurred.

Figure 8:
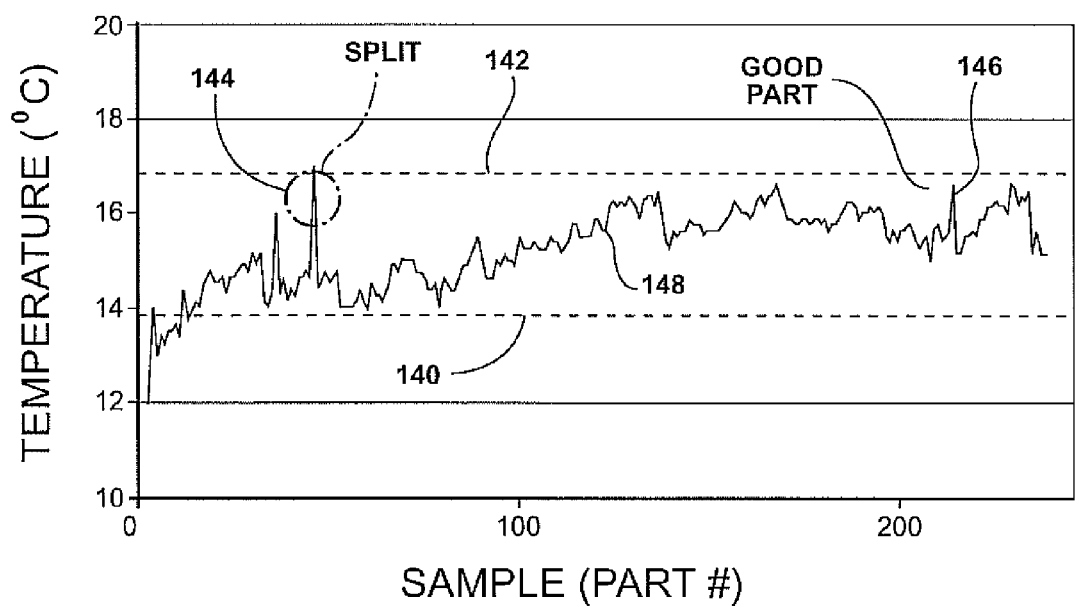
FIG. 8 illustrates an equipment temperature increase causing subtracted data without gradient determination to become unreliable.

FIG. 8 illustrates the effect of equipment temperature increases on subtracted data. In this case, a reference image is subtracted from an acquired image. As the temperature of the equipment increased during a production run (left to right, as the sample part number increases), the temperature difference between the acquired data and reference data tended to generally increase as indicated by a general rise in the curve 148. A threshold was set (the upper dashed line 142) for acceptable panels, and indicated a defect at 144. However, due to the long term thermal drift, it was not possible to select a single threshold capable of reliably indicating a problem without also causing a risk of false positives later in the production run, for example near 146, when temperature differences tended to be higher even for acceptable parts.

Figure 9:
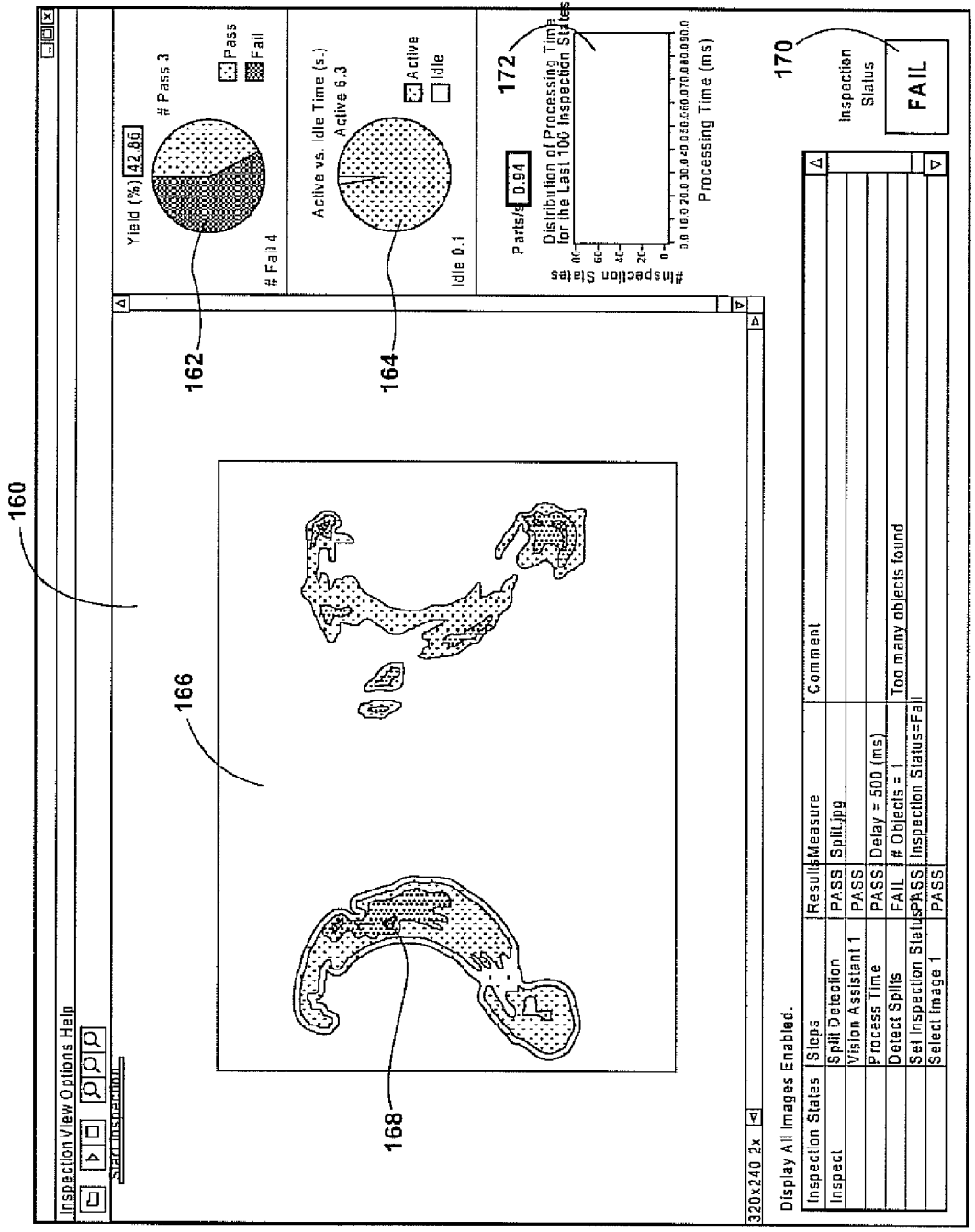
FIG. 9 illustrates an example display output.

FIG. 9 illustrates an example display output, which is not intended to be limiting. The image processing was performed by a computer having a memory (used to store a reference image), a clock, a processor, a data input port connected to a thermal camera, and a display output connected to the display shown at 160. The display shows the difference gradient image 166 of the part (the thermal gradient of the acquired thermal image subtracted by a reference image), with a defect highlighted at 168. Graphical representations of part yield 162, active versus idle time 164, distribution of processing time the last 100 inspection states 172, and pass/fail indication 170 (in this example, failure due to defect 168), are shown. In this case, a single split defect was found, which is unacceptable and the part is rejected. In some applications, a predetermined number of defects, type of defects, area of defect, or other parameter may be used, in which some degree of defective nature is considered acceptable.

Other possible aspects of some examples of the invention are now discussed.

The camera may be a thermal camera. Preferably, the camera is positioned to acquire thermal image from the part after completion of the forming process, or at some other part of the process that is of interest. In the case of stamping, this may be soon after the part is released from the die. In some experiments, a thermal image was acquired from the formed part in less than approximately 3 seconds after the stamping process, in some examples less than 1 second, such as approximately 0.5 seconds.

In some examples, more than one camera may be used to obtain a field of view covering an entire part. Image data may be formed as a combination of data obtained from more than one camera.

Image data acquisition may be time gated using a signal obtained from the processing equipment. For example, an electrical signal from a press, associated interlock, optical sensor detecting a beam broken by the press, or any other suitable source may be used to trigger image data acquisition.

In some cases, a plurality of thermal images may be acquired from a formed part after processing is complete. The time-dependence of gradient image data may provide a diagnostic indication of the type and extent of defect. In some examples, data may be extrapolated back from time(s) of image acquisition to the time of part formation, so as to provide a thermal image representative of the part at the time of formation.

Examples of the present invention can be used for forming processes, such as metal forming processes, in particular forming processes such as stamping, rolling, bending, drawing, extrusion, spinning, roll formation, sheet forming, forging and the like.

Examples of the present invention may also be used to detect defects or other problems during other processes, such as machining of parts, such as drilling, turning, milling, grinding, sawing, cutting, and the like. A thermal image of a machined part during a machining process may be compared with a reference image of a similar part undergoing a defect-free process, and defects, tears, and the like in the part can be detected using the gradient temperature difference image as described in the examples above.

In some examples, a sequence of time-dependent images or video may be used as acquired image and/or the reference image. For example, gradient difference temperature images may be determined at different times in a process, or as a video output, using a plurality of acquired images and at least one reference image.

An example image processor receives image data from one or more cameras, compares the acquired image data with reference image data so as to obtain difference image data (for example, subtracted image data), and determines thermal gradient image data from the subtracted data. The thermal gradient data is used to assist detection of defects, for example by comparison with one or more threshold values.

For example, there may be a threshold thermal gradient above which a part is rejected. There may be one or more lower thresholds that result in other actions, such as visual inspection, calibration of reference data, acquisition of new reference data, and the like.

The output device may include a visually discernable device such as a display, lamp, or some combination thereof. An audible alert may be provided.

If a gradient image analysis is found to produce more false positives or negatives than acceptable (such as more than zero), a new reference image may be collected. The new reference image may be an image acquired previously for a part determined to be acceptable (e.g. defect free), or may be collected for the next acceptable part produced by the process.

Examples of the present invention include a software algorithm, executable by a processor to carry out a method according to an example of the present invention. Examples of the present invention also include memory devices used to store such an algorithm.

Software used to implement methods according to examples of the invention can be calibrated to an online part. In some examples, volume accuracy of a method may be improved by recalibration, for example by obtaining a reference image at intervals. For example, a part may be examined by another method (such as visual inspection) at production intervals, and if the part is found to be acceptable, the just acquired image can be used as a reference image.

Hence, examples of the present invention include a thermal gradient imaging process that compares a difference temperature gradient with a user defined maximum allowable difference temperature gradient. Difference temperature data can be obtained by subtracting a reference thermal image from a thermal image acquired for the part under evaluation. These example approaches are more reliable than comparing reference and formed part temperatures, for example due to the increase in the average temperature of the acquired images of formed part due to heating effects. During production, the tools used in metal forming processes may experience an increase in temperature which can then be transferred to the formed metal parts. The temperature of the part may become greater than the differences in temperatures observed between normal and defective parts that would eliminate the effectiveness of the defect detecting process. The use of the temperature gradient avoids this problem, and therefore is still an effective defect detecting means even after the metal forming tool has increased in temperature.

Examples of the present invention include image processing methods, such as an algorithm using image subtraction. Edge detection can be used for alignment of acquired and reference images before comparison (e.g. before subtraction of the reference image from the acquired image). Relative movement between part and camera can occur, for example due to vibration in a stamping press. These movements can be corrected for using image alignment, for example using edge detection within the acquired and reference images to align these images before a subtraction step.

Defect types may be identified by tracking the defect, through subsequent focal regions, to generate a defect signature and then comparing it with known defect profiles.

In some examples of the present invention, a calculated temperature distribution can be used as the reference image, in place of a reference image collected by the camera. A reference image may be obtained using a different camera from that used for the acquired image.

In some examples, the temperature of the equipment (such as die temperature) may be monitored, and the reference image adjusted according to the equipment and/or ambient temperature. For example, a constant temperature adjustment may be made to the reference image, or one of a plurality of reference images selected according to operating conditions such as equipment temperature.

In some examples, other filters can be used during image processing, such as high pass or low pass spatial filters, depending on the type of defect to be determined.

Example methods may further include aligning an acquired thermal image for a part and a reference thermal image, subtracting the reference thermal image from the acquired thermal image to obtain a difference thermal image, determining a gradient thermal image representing temperature gradients within the difference thermal image, and detecting defects using the gradient thermal image.

The invention is not restricted to the illustrative examples described above. Examples described are exemplary, and are not intended to limit the scope of the invention. Changes therein, other combinations of elements, and other uses will occur to those skilled in the art. The scope of the invention is defined by the scope of the claims.

Having described our invention, we claim:

1. A method of detecting defects in a metal part arising from processing of the metal part, the method comprising:

obtaining a reference image for the metal part before processing the metal part;

acquiring a thermal image of the metal part after processing the metal part;

determining a difference image by comparing the thermal image to the reference image, the difference image being related to temperature differences between temperature data represented by the thermal image and reference temperature data represented by the reference image;

determining a gradient image using the difference image, the gradient image representing temperature difference gradients within the difference image; and detecting defects in the metal part by displaying a filtered gradient image indicating regions of the metal part having a temperature difference gradient greater than a threshold value.

2. The method of claim 1, the method being a method of detecting defects in the metal part after a metal forming process.

3. The method of claim 1, the method being a method of detecting elongation defects and split defects in a stamped metal part.

4. The method of claim 1, wherein the reference image is a reference thermal image collected from a reference part after processing the reference part, the reference part being substantially defect-free.

5. The method of claim 1, the thermal image of the metal part being acquired within 5 seconds of processing the metal part.

6. The method of claim 1, further comprising aligning the thermal image with the reference image before determining the difference image.

7. The method of claim 1, the difference image being determined by subtracting reference temperature data represented by the reference image from temperature data represented by the thermal image.

8. The method of claim 1, further including rejecting the part if the temperature difference gradient is greater than the threshold value.

9. An apparatus for assisting the detection of defects in a metal part after processing the metal part, the apparatus comprising:

a camera, operable to acquire a thermal image of the metal part;

an image processing device, operable to compare the thermal image with a reference thermal image so as to determine a difference image, the difference image representing temperature differences between temperatures represented by the thermal image and reference temperatures represented by the reference image, the image processing device being further operable to determine a gradient image, the gradient image representing rates of change of temperature differences within the difference image, and further operable to determine a filtered gradient image, the filtered gradient image indicating regions of the metal part having a temperature difference gradient greater than a threshold value; and an output device, the output device providing a visual indication of the filtered gradient image so as to assist detection of defects within the metal part.

10. The apparatus of claim 9, the camera being a thermal camera.

11. The apparatus of claim 9, the image processing device being provided by an electronic circuit having a processor, a memory, a data input port, and a display output, the processor being operable to execute an algorithm, the algorithm determining the gradient image from the thermal image and the reference image, the electronic circuit receiving the thermal image from the camera using the data input port, the reference image being stored in the memory.

12. The apparatus of claim 9, the image processing device being provided by a computer.

13. The apparatus of claim 9, wherein the output device is a display, the gradient image being shown on the display.

* * * * *

UNITED STATES PATENT AND TRADEMARK OFFICE
CERTIFICATE OF CORRECTION

PATENT NO.       : 8,203,606 B2
APPLICATION NO.  : 12/267066
DATED            : June 19, 2012
INVENTOR(S)      : Thiago I. Avila et al.

It is certified that error appears in the above-identified patent and that said Letters Patent is hereby corrected as shown below:

In the Specifications

Col. 2, line 61: replace "rate of chance" with --rate of change--;

Col. 7, line 1: replace "toss of detail" with --loss of detail--.

Signed and Sealed this
Third Day of December, 2013

Margaret A. Focarino
*Commissioner for Patents of the United States Patent and Trademark Office*